(12) United States Patent
Zhao

(10) Patent No.: US 7,939,095 B2
(45) Date of Patent: May 10, 2011

(54) CROSSLINKED SILANE COATING FOR MEDICAL DEVICES

(75) Inventor: Jonathon Z. Zhao, Belle Mead, NJ (US)

(73) Assignee: Cordis Corporation, Miami Lakes, FL (US)

( * ) Notice: Subject to any disclaimer, the term of this patent is extended or adjusted under 35 U.S.C. 154(b) by 422 days.

(21) Appl. No.: 11/614,395

(22) Filed: Dec. 21, 2006

(65) Prior Publication Data

US 2008/0152929 A1    Jun. 26, 2008

(51) Int. Cl.
*A61F 2/02* (2006.01)

(52) U.S. Cl. ......... 424/426; 424/423; 424/424; 424/425

(58) Field of Classification Search .................. None
See application file for complete search history.

(56) References Cited

U.S. PATENT DOCUMENTS

| | | | |
|---|---|---|---|
| 4,291,095 A | 9/1981 | Chase et al. | |
| 4,733,655 A | 3/1988 | Smal | |
| 4,800,882 A | 1/1989 | Gianturco | |
| 4,886,062 A | 12/1989 | Wiktor | |
| 6,013,855 A * | 1/2000 | McPherson et al. | 623/23.76 |
| 6,015,855 A | 1/2000 | Dalton | |
| 6,844,028 B2 * | 1/2005 | Mao et al. | 427/384 |

FOREIGN PATENT DOCUMENTS

| | | |
|---|---|---|
| DE | 10 2005 018741 A1 | 10/2005 |
| EP | 0482480 A1 | 4/1992 |
| WO | WO 03/068289 A1 | 8/2003 |

OTHER PUBLICATIONS

Choi, I., et al. "Surface-Initiated Polymerization of L-Lactide: Coating of Solid Substrates with a Biodegradable Polymer", Macromol4cules (2001) vol. 34, pp. 5361-5363.
Jang, J., et al. "Corrosion Protection of Epoxy-Coated Steel Using Different Silane Coupling Agents", Journal of Applied Polymer Science (1999) vol. 71, pp. 585-593.
Kricheldorf, H., et al. "Poly(lactones). Polymerization Mechanism of Metal Alkoxide Initiated Polymerizations of Lactide and Various Lactones", Macrcomolecules (1988) vol. 21, pp. 286-298.
Wilson, B., et al. "A Recoverable Metal-Free Catalyst for the Green Polymerization of ε-Caprolactone", Macromolecules (2004) vol. 37, pp. 9709-9714.
Search Report for corresponding Application No. PCT/US07/84948 mailed Sep. 29, 2008.
Search Report for corresponding Application No. PCT/US07/84948 mailed May 27,2010.
Dubois, J., et al. "Aluminum Alkoxides: A Family of Versatile Initiators for the Ring-Opening Polymerization of Lactones and Lactides", Makromol. Chem. Macromol. Symp. 42/43, pp. 103-166 (1991).

(Continued)

*Primary Examiner* — Carlos A Azpuru

(57) ABSTRACT

Coatings are provided in which surfaces may be activated by covalently bonding a combination of silane derivatives (A) to the metal surface, covalently bonding a lactone polymer (B) to the silane derivative by in situ ring opening polymerization, and depositing at least one layer of a polyester (C) on the bonded lactone polymer. Biologically active agents or therapeutic compounds may be deposited with any of the polyester layers. Such coated surfaces may be useful in medical devices, in particular stents.

4 Claims, 6 Drawing Sheets

OTHER PUBLICATIONS

Inoue, S., "Coordination Ring-Opening Polymerization", Prog. Polym. Sci. vol. 13, p. 63-81 (1988).

Jonte, J., et al. "Polylactones. 4 Cationic Polymerization of Lactones by Means of Alkylsulfonate", J. Macromol. Sci-Chem, A23(4) pp. 495-514 (1986).

Kricheldorf, H., et al. "Anionic and Pseudoanionic Polymerization of Lactones—A Comparison", Makromol. Chem. Macromol. Symp. 32, pp. 285-298 (1990).

Lofgren, A., et al. "Recent Advances in Ring-Opening Polymerization of Lactones and Related Compounds", Rev. Macromol. Chem. Phys., C35(3), pp. 379-418 (1995).

* cited by examiner

CROSSLINKED SILANE COATING FOR MEDICAL DEVICES

FIELD OF THE INVENTION

This invention generally relates to at least one polymer layer covalently bonded to an activated surface. More particularly, a layer of polymer coating contains at least one biologically active agent that is applied to the surface of a medical device such as a stent. The invention further relates to methods of coating metals surfaces and preparing medical devices.

BACKGROUND OF THE INVENTION

Medical devices are commonly implanted into the body to treat various conditions. These medical devices are commonly constructed from polymers or metal, for example, a polymeric or metallic stent utilized to treat restenosis within a conduit of a body such as a blood vessel or biliary duct. The placement of metal or polymeric devices in the body can give rise to numerous complications. Some of these complications include increased risk of infection, initiation of a foreign body response resulting in inflammation and fibrous encapsulation, and/or initiation of a wound healing response resulting in hyperplasia and/or restenosis. These and other possible complications must be dealt with when introducing a metal or polymeric device into the body.

One approach to reducing the potential harmful effects is to improve the biocompatibility of the device. While there are several methods available to improve the biocompatibility of devices, one method that has met with limited success is to provide the device with the ability to deliver therapeutic and/or other biologically active agents to the vicinity of the implant. By so doing, some of the harmful effects associated with the implantation of medical devices are diminished. For example, antibiotics can be released from the device to minimize the possibility of infection, and anti-proliferative drugs can be released to inhibit hyperplasia. Another benefit is to localize the release of the therapeutic and/or biologically active agent(s) to the area where they are most needed. This avoids the spread of therapeutic and/or biologically active agent(s) to areas where they may prove toxic. It is also desired that therapeutic agents be released for long periods of time (days, weeks, or months) instead of an instantaneous release upon implant of the device.

Typically, a therapeutic agent is applied to the surface of a device via a polymer matrix. For example, in the case of a metallic device, a metal oxide is created to activate the surface. Thereafter a layer is formed on the activated metal surface that serves as a platform for a primer layer. A polymer blended with a biologically active agent or therapeutic agent that readily adheres to the primer layer may be employed. In many respects, the success of the polymer coatings depends on the nature of the contact between at least the polymer layer adjacent to the metal surface and the underlying metal surface. In particular, if the polymer cracks or peels away from the metal surface, the polymer layer having the biologically active agent will fail to perform.

Providing a device with a polymer containing a biologically active agent presents several challenges. When a polymer layer contains a biologically active agent the resulting polymer/biologically active agent composite may be prone to dilation, swelling, degradation, and/or volume changes because of interactions of the incorporated compound with aqueous environments of the body. Also, following the penetration of water into the polymer layer, dissolution of the compound and its subsequent release, may change the structure and porosity of the composite. In addition, due to penetration of water following drug dissolution, the polymer layer could be exposed to a mechanical stress due to osmotic forces. These effects may result in detachment of the polymer layer and its peeling from the metal surface.

U.S. Pat. No. 6,013,855—McPherson, describes methods for grafting hydrophilic polymers onto metal surfaces. This method included exposing the device surface to a silane coupling agent and causing the agent to be covalently bound to the hydrophilic device surface. The bonded silane layer was then exposed to a polymer such that the hydrophilic polymer became covalently bound to the silane layer. Of course, a device produced using this method will produce a primer layer that is unable to be derivatized and will remain on the device. In addition, the use of a hydrophilic polymer will expose the interface of the surface of the device and the polymer to osmotic forces that may cause separation.

The selection of the polymeric materials employed to coat the medical device is also an important consideration. There are only a small number of polymers possessing the physical characteristics that would render them useful for implantable medical devices since most devices undergo flexion and/or expansion during and upon implantation. Many polymers that demonstrate good drug release characteristics, when used alone as drug delivery vehicles, provide coatings that are too brittle to be used on devices that undergo flexion and/or expansion.

As stated above, biologically active and/or therapeutic agents are applied to medical devices to increase biocompatibility. Thus, in addition to creating a stable interface between the device and the polymer layer containing the biologically active agent, it is also desired to ensure any polymeric materials that may have an adverse affect on the body are removed. For example, after the therapeutic agent is released, several polymer layers or layers of other materials, including the primer layer will remain on the surface of the device. This can lead to undesirable complications such as restenosis and/or thrombosis. Other polymers can create an inflammatory response when implanted.

Insung S. Choi and Robert Langer, in "Surface-Initiated polymerization of l-Lactide: coating of solid substrates with a biodegradable polymer", Macromolecules (2001) 34, 5361-5363, discloses an in-situ polymerization of lactone polymers with stannous octoate ($Sn(Oc)_2$) as a catalyst on a solid surface such as metal modified with a hydroxyl or amine terminated silane derivative. International Publication No. WO20030068289—Rypacek et al, uses essentially the same strategy as in the Choi article to make a device having a silane layer which is modified to polymerize a composition such that a lactone polymer layer on the silane layer. This layer is bioabsorbable and provides a surface on which additional bioabsorbable polymer layers may be applied. Thus, these layers are removed after delivery of the therapeutic agent is complete. In creating the lactone polymer layer, however, a heavy metal based catalyst, such as stannous octoate, is employed and remains inside the coating. Certainly, biocompatibility is not optimized with heavy metals present in a patient's body. Moreover, the lactone polymer layer lacks adequate density. Thus, any additional polmer layer, for example, a polymer containing a biologically active agent and/or therapeutic agent, applied to the lactone polymer layer will not adhere optimally. This may cause separation of the layers causing a failure to deliver the biologically active and/or therapeutic agent.

It is desired to provide a coating for a medical device that is bioabsorbable and will provide a dense and stable platform onto which additional bioabsorbable layers may be applied.

SUMMARY OF THE INVENTION

The invention provides for a surface treatment and method for applying a surface treatment to a surface with an activating layer of crosslinked silane derivatives bound to the surface. The surface-activating layer is a siloxane polymer having one or both of sulfhydryl or epoxide terminal groups on the siloxane. A first layer of one or more lactone polymers is covalently bonded to the polymerized silane derivative. Additional polymer layers may be applied to the first layer. In one embodiment of the invention, the composition of the first layer or the additional layer(s), or both, includes one or more biologically active agents. The biologically active agent(s) is about 0.5 to about 60 percent by weight of the first or additional layer(s). The biologically active agent or therapeutic compound is released from the composition in an aqueous environment.

The first layer and the additional layer(s) have at least one layer of one or more lactone polymers. In the first layer, the lactone polymer may be a lactone homopolymer such as polyglycolide, poly(L-lactide), poly(D-lactide), poly(-caprolactone), poly(p-dioxanone), poly(dioxepanone), or a lactone copolymer such as poly(L-lactide-co-D-Lactide), poly(L-lactide-co-glycolide), poly(D-lactide-co-glycolide), poly(D, L-lactide-co-glycolide), poly(lactide-co-caprolactone), poly(lactide-co-dioxanone), poly(D,L-lactide), or poly(lactide-co-dioxepanone).

In the additional layer(s), the polyester polymer may be either a lactone homopolymer, a random copolymer, or a block copolymer with at least one polylactone block, while the other block or blocks of the copolymer may be a polyether, a poly(amino acid), a poly(acrylate), or a poly(methacrylate). In a preferred embodiment of the invention, the polymer of the additional layer(s) has a molecular weight of $10^3$ to $10^6$.

In various preferred embodiments, the first layer is a polylactide and the additional layer is one or more polymers such as poly(l-lactide), poly(glycolide), poly(lactide-co-glycolide) or poly(d,l-lactide), and the mole fraction of L-lactide structural units is in the range of either 0.5 to 1.0 or 0 to 0.5. The biologically active agent is about 0.5 to 60 percent of the total mass of polymer of the additional layer(s).

In another preferred embodiment of the invention, the composition of the inner additional sublayer is a semicrystalline polymer, or an amourphous polymer, or a semicrystalline mixture of polymers, and the outer additional sublayer comprises at least one amorphous polymer. The polymer of an inner additional sublayer may be a hydrophobic polymer which is either a lactone homopolymer, a statistical lactone copolymer, a lactone block copolymer, and the polymer of an outer additional sublayer is an amphiphilic copolymer of at least one of a statistical copolymer and a block copolymer of lactones and ethylene oxide.

Yet another embodiment of the invention includes a method of coating a surface such as a metal, ceramic or glass surface. The method includes reacting the surface with a silane-based activating agent to form a surface having an activated layer with at least two functional terminals, one of which functions as a non-metallic in situ catalyst, for example one not containing tin. At least one lactone monomer or dimer is polymerized employing ring opening polymerization to form the first polymer layer on the surface. Additional layer(s) may be deposited onto the first polymer layer, for example, by applying at least one solvent solution comprising a polymer on the first layer and evaporating the solvent to form at least one additional layer adhered to the first layer.

The preferred silane-based activating agent is a silane derivative of general formula:

$(RO)_3Si(CH_2)_nX$

RO is a hydrolysable group, such as methoxy, ethoxy, or acetoxy, and X is an organofuntional group, such as amino, methacryloxy, epoxy, etc. R can be independently selected from substituted alkyl, substituted alkenyl, substituted alkynyl, substituted aralkyl, substituted heteroaryl, and substituted alkoxy, with the proviso that R is preferably the same for all 3 R groups. N is an integer ranging from 1 to 10. Other similar space between the silicon atom and the organofucntional group X can contain additional structural element such as ether, ester, etc. provided that they do not interfere with the silylating process or the subsequence reactions.

A silane-coupling agent acts as an interface between an inorganic substrate (such as glass, metal or mineral and an organic material (such as an organic polymer, coating or adhesive) to bond, or couple, the two dissimilar materials. Silane coupling agents that contain three inorganic reactive groups on the silicon (usually methoxy, ethoxy or acetoxy) will bond well to the metal hydroxyl groups on most inorganic substrates, especially if the substrate contains silicon, aluminum or a heavy metal in its structure. The alkoxy groups on silicon hydrolyze to silanols, either through the addition of water or from residual water on the inorganic surface. The silanols coordinate with metal hydroxyl groups on the inorganic surface to form an oxane bond and eliminate water.

In yet another embodiment the silane-based activating agent is applied in a solution or in a vapor phase to form an activating layer bound to the surface. The oxidation of the sulfhydryl group to sulfonic acid group can be achieved by adding a solution containing hydrogen peroxide in methanol to the activated surface. The derivatization of the epoxy group is achieved by adding a bifunctional agent such as a diamine or a diol to the solution containing the activated surface with epoxy terminal groups. The original epoxy group will be transformed to a bifunctional group of a diol if a diol is used for the conversion, or a bifunctional group comprising a hydroxyl and an amine group if a diamine is used for the conversion. This transformation serves to double the density of the functional groups on the surface. The final silanized surface can be then rinsed with a common organic solvent such as tetrahydrofuran to remove excess reagents before the first polymer conjugation process.

Both the hydroxyl and amine group serves as the initial point for the ring opening polymerization with the nearby sulfonic acid serving as a metal free in situ catalyst of the ring opening polymerization. Formation of a first layer by lactone rign opening polymerization includes immersing an activated surface with both sulfonic acid group and multiple hydroxyl and amine groups in a lactone dimer or monomer solution, or a lactone dimer or monomer melt at a temperature sufficient to keep the lactone in the molten state for a time sufficient to allow the in-situ ring opening polymerization of the lactone on the activated surfade to form the first lactone polymer layer.

Formation of an additional layer includes the deposition of a solvent solution containing the polymer onto the first layer by bringing a metal surface having the activation layer and first layer into contact with a polymer solution by dipping the surface into the solvent solution or spraying, casting, pouring or spreading the solution onto the surface, and evaporating the excess solvent. The solvent solution may contain one or more biologically active or therapeutic compounds. In certain embodiments, the solvent is an aprotic solvent such as an ether, ketone; aromatic hydrocarbon and a mixture of these solvents.

In yet another embodiment, the invention provides for a medical device having a metal surface with a metal-activating layer of polymerized silane derivatives covalently bonded to the metal surface, a first layer of a polylactone covalently bonded to the polymerized silane derivatives, and a additional layer of a polymer adhered to the first layer, where the additional layer has a biologically active agent(s) and/or therapeutic agents releaseably associated with the polymer. The biologically active agent(s) and/or therapeutic agents may be about 0.5 to 60% by weight of the additional layer. The medical device may comprise, for example, a stent, vascular graft tubing, a blood oxygenator, an intravascular balloon, a catheter, an implantable pulse generator, an electrode, an electrical lead, sutures, a soft or hard tissue prosthesis, or an artificial organ.

DETAILED DESCRIPTION OF THE INVENTION

Figure 1:
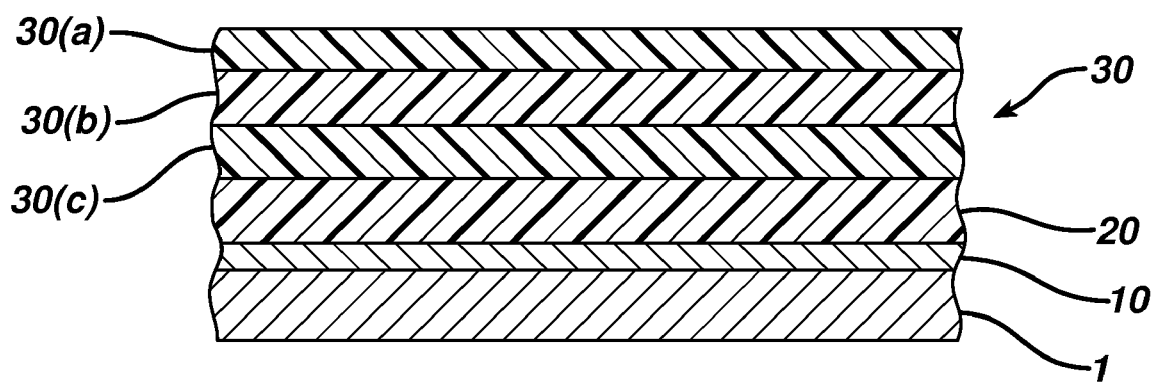
FIG. 1 is a schematic representation of a surface coated in accordance with the present invention.

Polymer coating can improve the performance of a medical device by providing a biocompatible interface between the metal surface and the surrounding tissue, while the biological response of the organism, namely the local response of the surrounding tissue, can be modulated by sustained release of a suitable biologically active agent(s). A thin polymer layer, that does not significantly affect mechanical properties of the device and that provides for a long-lasting matrix reservoir for a biologically active agent(s) to be released in a controlled manner, can be produced by a successive deposition of chemically compatible polymers on the metal surface of the implantable device.

An activating silane derivative interfacing the metal surface is bound to the metal surface to activate the surface and provide for suitable functional groups. Second, a polymer (first) layer is bound, for example covalently, to the activating layer. The covalent bond of the first polymer layer provides for adhesion of any subsequent polymer layers to the surface of the device. This allows for a thin, durable and contiguous film having an adjustable and repeatable release performance. This method is applicable for use with biocompatible, medically applicable polymers, thus making the method suitable for coating medical devices.

As used herein, the terms listed below have the following definitions:

"Optional" or "optionally" means that the subsequently described event or circumstance may or may not occur, and that the description includes instances where said event or circumstance occurs and instances in which it does not.

The term "homopolymer" means a polymer derived from one species of monomer.

The term "copolymer" means a polymer derived from more than one species of monomer.

The term "random copolymer" means a copolymer consisting of macromolecules in which the sequential distribution of the monomeric units obeys known statistical laws, e.g. the sequential distribution of monomer units follows Markovian statistics.

The term "block copolymer" means a polymer composed of macromolecules consisting of a linear sequence of blocks, wherein the term "block" means a portion of macromolecule comprising many constitutional units that has at least one feature that is not present in the adjacent portions.

The term "polymer matrix" refers to all of the polymer layers or sublayers on the metal surface. This can include activating, first, additional, and/or barrier layers.

The term "amphiphilic copolymer" means a polymer containing both hydrophilic (water-soluble) and hydrophobic (water-insoluble) segments.

The term "polyester" means a polymer with structural units connected by ester bonds, comprising polyesters obtained from dicarboxylic acids and dials, or from hydroxyalkanoic acids by polycondensation, and includes polylactones obtained by ring-opening polymerization of lactones, such as polyglycolides polylactides, polycaprolactone and related copolymers.

The term "metal" means surfaces made of, for example, stainless steel, titanium or tantalum with oxide groups on their surface, as well as other surfaces made of, for example, polymers or glass, with hydroxyl groups or other functional groups that can be transformed to hydroxyl groups on their surfaces. The surface may be of any shape and may be a part of any medical devices. Examples of such devices include both implantable or extracorporeal devices such as vascular graft tubing, blood oxygenators, intravascular balloons, catheters, implantable pulse generators, electrodes, electrical leads, stems, sutures, soft or hard tissue prosthesis, artificial organs and the like. Further, there are likely to be many applications for the coated metal outside the medical field. Accordingly, it will be appreciated by those skilled in the art that the invention described may be applied to many medical devices and in fields outside of medicine where a polymer coated metal surface of the invention may be useful.

The words "flexion" and "expansion" as used herein with regard to implantable devices will refer to a device, or portion thereof, that is bent and/or expanded either in the course of its placement, or thereafter in the course of its uses in vivo Stents are designed to mechanically prevent the collapse and reocclusion of the coronary arteries. The coating composition can also be used to coat stems, which are typically prepared from materials such as stainless steel, cobalt comium or tantalum or from a polymer, polymer blend, or a polymer/polymer blend having additives and agents. A variety of stent configurations are known including but not limited to shape memory alloy stems, expandable stents and stents formed in situ e.g., either self-expanding stents (such as the Wallstent variety), or balloon-expandable stents (as are available in a variety of styles, for instance, Gianturco-Roubin, Palmaz-Shatz, Wiktor, Strecker, ACS Multi-Link, Cordis, AVE Micro Stent). Other suitable metals for such stents include gold, molybdenum-rhenulm alloy, platinum-iridium alloy and combinations thereof. See, for example, U.S. Pat. Nos. 4,733,655, 4,800,882 and 4,886,062, all of which are incorporated by reference in their entirety.

The polymer coating or coating composition is applied to a surface 1 and can be composed of several layers. Referring now to FIG. 1, the surface has a first coat 10, referred to herein as the activating layer that is composed of silane derivatives bound to the surface 10. If surface 10 is metallic, it is first oxidized. A second layer 20, which may be a first polymer layer, is composed of a polylactone covalently bonded to the multi-functional terminals of the silane derivatives in layer 10. Additional layer(s) 30 may be deposited on layer 20. The additional layer(s) 30 may optionally be composed of one or more sublayers of the same or different polymers.

Layer 20 and the additional layer(s) 30 may optionally contain one or more biologically active and/or therapeutic compounds, for example, a drug that is releasably dispersed in the matrix of a polymer coating comprising layer 30. Once the coated surface 1 is placed in an aqueous environment, typically body fluids, such as blood, lymph or extracellular fluids, the agent or biologically active compounds are released into the surrounding tissue or environment. The composition of the layer 20 and the additional layer(s) 30 may, for example, be adjusted to provide for a controlled release of these compounds into a surrounding aqueous medium and/or to modify the tissue reaction to the presence of the device, for example, to make the surface thromboresistant. The coated surface 1 may be composed of two or more; sublayers with different functions, optionally a top layer 40 may function as a barrier or skin layer.

The biologically active and/or therapeutic agents useful in the present invention include virtually any substance that possesses desirable characteristics for application to the implant site. As used herein "biologically active agent and/or therapeutic agent" refers to a single agent or multiple agents. For example, it is contemplated that one or more biologically active and/or therapeutic agents may be releasably associated with the polymers on the metal surface. These agents include, but are not limited to: thrombin inhibitors, antithrombogenic agents, thrombolytic agents (e.g. factor Xa inhibitors), fibrinolytic agents, vasospasm inhibitors, calcium channel blockers, vasodilators, antihypertensive agents, antimicrombial agents, antibiotics, inhibitors of surface glycoprotein receptors, antiplatelet agents, antimitotics, microtubule inhibitors, anti secretory agents, actin inhibitors, remodeling inhibitors, antisense nucleotide, anti metabolites, antiproliferatives (e.g. E2F antisense compounds, Rapamycin (sirolimus), tacrolimus, Taxol, paclitaxol, Cyclin Dependent Kinase inhibitors) anticancer chemotherapeutic agents, anti-inflammatory steroid or non-steroidal anti-inflammatory agents, immunosuppressive agents, growth hormone antagonists (e.g. PDGF receptor tyrosine kinase inhibitors), growth factors, dopamine agonists, radiotheraputic agents, peptides, proteins, enzymes, extracellular matrix components, ACE inhibitors, free radical scavengers, chelators, antioxidants, antipolyermases, ribozymes, antiviral agents, photodynamic therapy agents, and gene therapy agents such as 6-ylamino]-methyl}-benzoic acid.

The invention provides for the formation of the first layer covalently bonded, grafted, or attached, to the surface-activating layer. A pretreatment of a surface, such as a metal surface, by an oxidizing agent prior to application of functional silane derivatives, for example, the treatment of the metal surface by an oxidizing agent or a commercially available cleaning agent such as ENPREP can be used as a part or whole of the cleansing procedure.

The grafted first polymer layer is formed by the in-situ ring opening polymerization of lactone monomers initiated by suitable functional groups of the silane derivatives on the activating layer and catalyzed by the sulfonic acid tethered to the silane derivatives. Suitable functional groups for initiating the grafting polymerization of lactones ("initiating functional groups") can be created on surfaces through the reaction of a surface, for example a metallic surface, with selected silane derivatives, referred to herein as functional silane derivatives. Typical functional silane derivatives can be found in "A guide to silane selection" published by Dow Corning (reference 1). Other suitable functional silane derivatives can be found in GELEST Catalogue 2000: Silanes, Silicones and Metal-Organics. Gelest, Inc., Dr. Barry Arkles, Tullytown, Pa., USA. I To treat metal surfaces, a functional silane derivative can be applied in solution or in a vapor phase. A variety of solvents and solvent compositions can be used. In this respect, numerous references are available, teaching the use of silane derivatives in sol-gel processes and as adhesion promoters in corrosion protection. For a review of this art see for example, ller, R. K. The Chemistry of Silica, Wiley, New York, 1979; Brinker, J., Scherer, G. W., Sol-Gel Science: the Physics and Chemistry of Sol-Gel Processing, Academic Press, New York, 1990; Jang, J., Kim, E. K. Corrosion Protection of Epoxy-Coated Steel Using Different Silane Coupling Agents, J. Applied I Polym. Sci. (1999), 71:585; Insung S. Choi and Robert Langer, Surface-Initiated polymerization of l-Lactide: coating of solid substrates with a biodegradable polymer, Macromolecules (2001) 34, 5361-5363; Benn C. Wilson and Christopher W. Jones, A Recoverabl, Metal-Free Catalysts for the Green Polymerization of ipsilon-caprolactone, Macromolecules, (2004) 37, 9709-9714; RYPÁCEK; Frantisek et. al, Polymer coating for medical devices, WO2003068289A1, Each of these references are incorporated herein by reference in its entirety.

Following the silylation of the surface, a first lactone polymer layer is conjugated to the activated surface. To apply the polymer of the first layer, a first or grafting reaction is carried out by exposing the functional silane derivative-activated surface to a solution of lactone in a suitable aprotic solvent, or to a lactone in bulk. In the initiation reaction of the grafting polymerization, the first lactone dimer or monomer forms a covalent bond with the multiple functional terminals of the functional silane derivatives bound to the metal surface.

In subsequent steps, the polylactone chain propagates by a stepwise addition of lactone dimer or monomer. The growing polymer chains thus remain covalently bound to the surface through its initial structural units. The chemical mechanisms that apply in the polymerization grafting used in this embodiment are analogous to those that apply in the ring-opening polymerization of lactones in bulk or a solution. The field of lactone polymerization either in bulk or a solution is well described in numerous literature and the principles of these reactions are known to those skilled in the art.

Examples of the most frequently used polymerization reactions can be found in Dubois, P. et al., Aluminium Alkoxides: A Family of Versatile Initiators for the Ring-Opening Polymerization of Lactones and Lactides, Makromol. Chem., Macromol. Symp. (1991) 42/43:103-116; Inoue, S., Coordination Ring-Opening Polymerization. Prog. Polymer. Sci. (1988) 13:63-81; Jonte, J. M. et al., Polylactones.4. Cationic Polymerization of Lactones by Means of Alkylsulfonates. J. Macromol. Sci.-Chem. (1986) A23:495-514; Kricheldorf, H. R. et al., Anionic and Pseudoanionic Polymerization of Lactones-a Comparison. Makromol. Chem., Macromol. Symp. (1990), 32:285-298; Kricheldorf, H. R. et al., Poly(Lactones). 9. Polymerization Mechanism of Metal Alkoxide Initiated Polymerizations of Lactide Various Lactones, Macromolecules (1988) 21:286-293; and Lofgren, A. et al., J. M. S.-Rev. Macromol. Chem. Phys. (1995) C35:379-418, Insung S. Choi and Robert Langer, Surface-Initiated polymerization of l-Lactide: coating of solid substrates with a biodegradable polymer, Macromolecules (2001) 34, 5361-5363; Benn C. Wilson and Christopher W. Jones, A Recoverabl, Metal-Free Catalysts for the Green Polymerization of ipsilon-caprolactone, Macromolecules, (2004) 37, 9709-9714; RYPACEK; Frantisek et. al, Polymer coating for medical devices, WO2003068289A1, each of which are incorporated by reference in their entirely Suitable monomers and dimers in grafting ring polymerization of the first polymer layer are lactones. Typical examples of lactones include four to seven-membered lactones, for example, the families of compounds comprising oxetan-2-one and 4-alkyl-oxetan-2-one, dihydrofuran-2-one and 5-alkyl-dihydrofuran-2-one, tetrahydropyran-2-one and 6-alkyl-tetrahydropyran-2-one, oxepan-2-one and 7-alkyl-oxepan-2-one, 1,4-dioxan-2,5-dione, 3,6-alkyl-1,4-dioxan-2,5-dione, 1,3-dioxopan-2-one, 1,3-dioxan-2-one, 1,3-dioxolan-2-one, 1,5-dioxepan-2-one, 1,4-dioxepan-2-one, 1,3-dioxepan-4-one, and their substituted analogues, wherein the alkyl is C1-C10 alkyl or a substituted alkyl.

In one embodiment of the invention the lactone monomer comprises lactide (3,6-dimethyl-1,4-dioxane-2,5-dione) in its various enantiomeric forms (L-lactide, D-lactide, meso-lactide and their mixtures), glycolide (1,4-dioxane-2,5-dione), and c-caprolactone. For the first layer, combinations of lactone monomers may be used to provide for grafting copolymerization. These copolymers can be made available with different ratios of the co-monomers. Both the homopolymers and copolymers can be used in different molecular-weight ranges. Preferably, the lactone copolymer includes one of poly(L-lactide-co-D-Lactide), poly(L-lactide-co-glycolide), poly(D-lactide-co glycolide), poly(D,L-lactide-co-glycolide), poly(lactide-co-caprolactone), poly(lactide-co dioxanone), and poly(lactide-co-dioxepanone).

Typical examples of aprotic solvents for carrying out the grafting reaction in solution include ethers (e.g., tetrahydrofuran, dioxane, di(ethylene glycol), diethyl ether), ketones (e.g. ethylmethyl ketone, diisobutyl ketone) and aromatic hydrocarbons (e.g. toluene, xylene), and mixtures of these solvents. Those skilled in the art can readily identify other solvents that would be useful for the grafting reaction.

The grafting ring polymerization at the functional terminals of the silane derivatives can be carried out in the absence of solvent, i.e., in the mixture formed by a lactone in bulk. In this mode of the invention, the temperature of the reaction is preferably such as to keep the lactone in a liquid state, such as above the melting temperature of the lactone. The reaction in lactone melt is carried out for the time necessary to form a first layer of a desired thickness. After carrying out the reaction for a given time, the surface is removed from the melt, the residual lactone is washed from the surface by a suitable solvent and the grafted surface is dried.

The covalently grafted polymer first layer is firmly bonded to the surface. As a result, this first covalent bonded polymer layer is resistant to removal by treatment with solvents. Thermodynamically solvents, however, can penetrate into the grafted polymer layer, causing the polymer chains to expand and thus become capable of adsorbing or accumulating compounds from solutions. The adsorbed or accumulated compounds can be either biologically active agents or molecules of another polymer that have a similar or a compatible chemical structure or that are miscible with the grafted polymer. These features of the grafted polylactone layer can be employed either for direct incorporation of biologically active agents to be released from the layer or for the design and attachment of other subsequent, well adherent, high-capacity polymer layers incorporating the agents.

When the polylactone first layer, grafted to the surface 1, is soaked in a solution of the biologically active agent in a solvent appropriate for a given polylactone, the solvent swells the first polymer layer making it possible for the biologically active agent to penetrate the first polymer layer. After the solvent is stripped off by evaporation, which can be either spontaneous or assisted by the application of vacuum, the biologically active agent, being less volatile than the solvent, is embedded in the polymer, the chains of which have condensed, thus becoming closely packed into a compact matrix upon removal of solvent. Later, when the surface is put into an environment that is not a good solvent for the polymer, such as the aqueous environment of tissue fluids, the condensed polymer chains prevent the molecules of the agent from being rapidly dissolved or diffused into the aqueous medium. This action extends the time period within which the agent is released.

According to another embodiment of the invention, the polylactone first layer grafted to the surface is soaked in a solution formed by a solvent for polylactone, a biologically active agent, and a polymer that is chemically compatible or miscible with the first layer. The polymer deposited from the solution on the top of the grafted first layer forms the additional layer on the surface. When the surface is soaked in the solution, the solvent swells the grafted polymer first layer and the polymer molecules that are to form the additional layer penetrate the swollen grafted first layer and entangle with the grafted chains. Additionally, the biologically active agent in solution may become embedded in the first layer.

In practice, the solution containing the polymer of the additional layer is applied to form a liquid film on the top of the grafted first layer surface. After the solvent has been evaporated from the solution, the solidified polymer film of the additional layer will become well joined with the underlying grafted first layer due to mutual entanglements of polymer chains. Layers of polymers of various controllable thickness and composition can be applied to the anchoring grafted first layer to form sublayers of the additional layer. Biologically active agents contained in the solution with the polymer remain embedded in the solidified polymer additional layer film. It is also possible to soak the polylactone first layer grafted to the metal surface in a solution of a biologically active agent, using a good solvent for both the grafted polylactone and the biologically active agent. The biologically active agent will penetrate into the grafted polymer first layer that is being swollen by the solvent and, after evaporation of the solvent, the biologically active agent will then remain embedded in the grafted polymer first layer.

Biologically active agents can be released from the solidified film of binder and/or additional layer into the aqueous environment by their gradual dissolution and diffusion through the polymer matrix. This release may also be accomplished by polymer degradation alone, or in addition to the diffusion of the biologically active agent through the polymer matrix. By controlling the thickness and composition of the polymer layers (e.g., first and additional), the capacity of the system for the loaded biologically active agent and the rate of its release can be controlled. Accordingly, the biologically active agent is releasably associated with the polymer. When the coated metal surface is used as an implantable medical device, the biologically active agent can be locally released from the polymer matrix in a controlled manner into a patient receiving the medical device.

As described above, a stable and well adherent polymer matrix can be achieved through various combinations of the compositions of the additional layer and the first layer using a variety of lactone polymers and copolymers by taking into account the chemical compatibility or miscibility of the polymers of both layers. In various embodiments of the invention, the physical properties of the polymer coating matrix can be modified while maintaining the compatibility of the first layer and the additional layer. The composition of the polymers in the layers can be adjusted by using either a chemical modification, such as statistical and block copolymers, or a physical modification, such as blends or composites.

The polymers used for formation of the additional layer include lactone homopolymers, examples of which include poly(L-lactide), poly(D-lactide), polyglycolide, poly(-caprolactone), poly(p-dioxanone), poly(dioxepanone), poly(trimethylene carbonate) statistical copolymers of lactones, examples of which may include poly(L-lactide-co-D-Lactide), poly(lactide-co-glycolide), poly(D,L-lactide), poly(lactide-co-caprolactone), poly(lactide-co-trimethylene carbonate) and other combinations of lactones that can be typically derived from lactone monomers. These copolymers can be made with different ratios of the co-monomers. Both the homopolymers and copolymers can be used in different molecular-weight ranges.

The additional layer can also include a block copolymer containing at least one polylactone block. The other blocks of the copolymer can be based on polylactone or another chemical structure such as polyether, poly(amino acid), poly(acrylate), poly(methacrylate), polybutadiene, polyisoprene, etc. Typical examples of compositions of suitable block copolymers comprise polylactide/polycaprolactone, polylactide/poly(ethylene oxide), polycaprolactone/polybutadiene, polycaprolactone/poly(ethylene oxide), polylactide/poly(amino acid). The block copolymers can exhibit different ratios of block lengths, different numbers of blocks, and different molecular weights.

It is anticipated that the properties of copolymers may vary with different ratios of co-monomers in the copolymers as well as they may vary with molecular weight. The invention is not limited to any particular copolymer composition or a molecular weight range. In addition to changing the chemical constitution of the polymer molecules, the properties of polymer films formed can be modified also by blending different types of polymers, i.e. homopolymers, statistical and block copolymers.

There are many ways to apply the polymer solution to become the additional layer on the polymer-grafted first layer surface of a metal article. Procedures commonly known in coating applications can be used as long as they provide for good wetting of the first layer surface by the polymer solution. Preferably the application procedure will allow for the control of the parameters of the polymer layer such as layer composition, thickness, and integrity. Thus, the polymer solution can be applied on the first layer surface by dipping the surface to be coated in the polymer solution, by spraying the polymer solution on the first layer surface, by pouring or spreading the solution onto the first layer surface, or any other technique known to those skilled in the art. After the solution is applied to the first layer surface, excess solvent is evaporated. Various means to control the amount of solution remaining on the first layer surface before and during evaporation of the solvent can be used to control the thickness and homogeneity of the additional layer. These procedures include spreading the solution and stripping its excess by a centrifugal force, spreading and removing the excess solution by a spreading tool, dosed spraying, and those procedures that are generally known in the art of polymer coating.

In a preferred embodiment of the invention, the compositions of the grafted first layer and the additional layer are chosen such that at least one polymer component of the additional layer is well compatible with the polymer of the first layer. Compatibility between the layers improves the wetting of the first layer by the solution of the additional layer and facilitates the formation of a contiguous and well-adherent polymer matrix. Thus, the polymer film of the additional layer may be designed so that it has the desired composition, thickness and physical properties, such as morphology, phase structure, glass transition, and crystallinity, while being capable of being applied in a simple coating technique.

According to another embodiment of the invention, the polymer solution of the additional layer may contain one or more biologically active agents that is/are released when a device with the polymer matrix is placed in an appropriate aqueous environment. The biologically active agent may be either dissolved in the solution containing the polymer, or it can be dispersed in the solution of the polymer in a form of solid particles. In either case, the biologically active agent will become incorporated in the polymer film during the solidification of the polymer layer by solvent evaporation.

The rate of the release of the biologically active agent can be controlled through the composition and other parameters of the polymer additional layer. The parameters such as layer thickness, morphology, phase structure, hydrophobicity, degree of hydration, the ratio of crystalline and amorphous phases, glass-transition temperature of the polymer are relevant to release control. These parameters can be controlled through the selection of polymers and their application procedures.

Further, other blends can be used in additional or optional barrier layers. While polyesters like polylactide (PLA) and polycaprolactone (PCL) are rather hydrophobic polymers, exhibiting a low degree of hydration, poly(ethylene oxide) (PEO) is a hydrophilic polymer and is soluble in water. Thus a polymer film composed of polylactide and a polylactide/poly(ethylene oxide) block copolymer can form a two phase system with a hydrophobic phase, rich in PLA, and a hydrophilic phase, rich in PEO. The degree of hydration of the polymer and, consequently, the permeability of the polymer film for water and incorporated hydrophilic biologically active agents can be increased by increasing the fraction of the hydrophilic phase, such as PLA/PEO block copolymer, in the blend. Thus, through the variation of the PLA/PEO copolymer in the film the release rate of certain biologically active agents can be controlled. Similarly, depending on the degree to which a biologically active agent is hydrophilic or hydrophobic, other combinations of polymers can be used to control the release rate of biologically active agents.

In a polymer matrix with more than one additional layer, the outermost additional sublayer may function as a skin, i.e., this layer either does not include the biologically active agent or its concentration in the skin layer is significantly lower than that in the underlying additional sublayers. The skin layer can be used to further control the release of the biologically active agent. Additional skin layers may be applied to improve the biocompatibility to the device.

The polymer layers may contain up to about 60% of the biologically active agent by weight, depending on the physical properties of the biologically active agent, such as its solubility in water, its crystalline forms and compatibility with the polymer matrix forming the layer. It is anticipated that a content of biologically active agent close to the upper limit of this range can be more easily achieved with low-solubility compounds, which at the same time exhibit a high adherence to the polymer of the additional layer. On the other hand, biologically active agents with high solubility or pure miscibility with the polymer matrix will need to be in the lower portion of this range. A typical range of the biologically active agent content for most applicable compounds will be between 1 to 50% by weight. The overall weight of the coating (polymer matrix plus biologically active agent) on the device is typically very important. Within the constraints of adequate clinical efficacy, the total dose of polymer plus a drug should be minimized to avoid long term side effects, including delayed endothelialization of the arterial wall, prolonged inflammation caused by the presence of the polymers and the degrading oligomers and final metabolites.

The weight of the coating attributable to the biologically active agent can be in the range of about 0.1 microgram to about 500 micrograms of biologically active agent per $cm^2$ of the gross surface area of the device. More preferably, the weight of an active drug or a biologically active agent in the coating is between about 1 microgram and about 100 micrograms per $cm^2$ of the nominal surface area of the device. This quantity of biologically active agent is generally required to provide adequate activity under physiological conditions.

The coating (polymer matrix plus biologically active agent) thickness of a presently preferred composition will typically be in the range of about 0.01 micrometers to about 100 micrometers. This level of coating thickness is generally required to provide an adequate density of biologically active agent to provide adequate activity under physiological conditions and minimize the unwanted reactions from the surrounding tissue to the degrading polymer. A more preferred thickness of coating is between 0.01 μm to about 10 μm.

Figure 2:
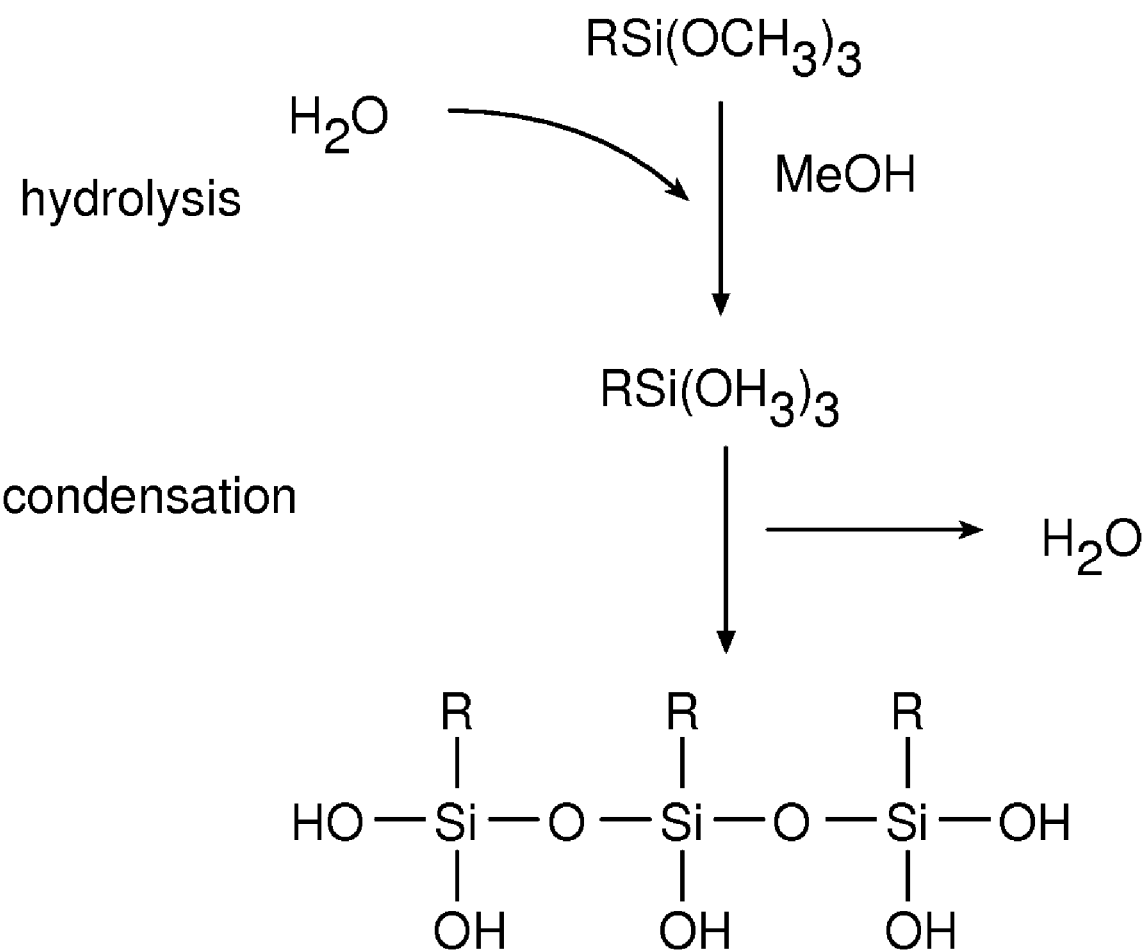
FIG. 2 is a schematic representation of the hydrolysis of alkoxysilane in the activation process.
Figure 3:
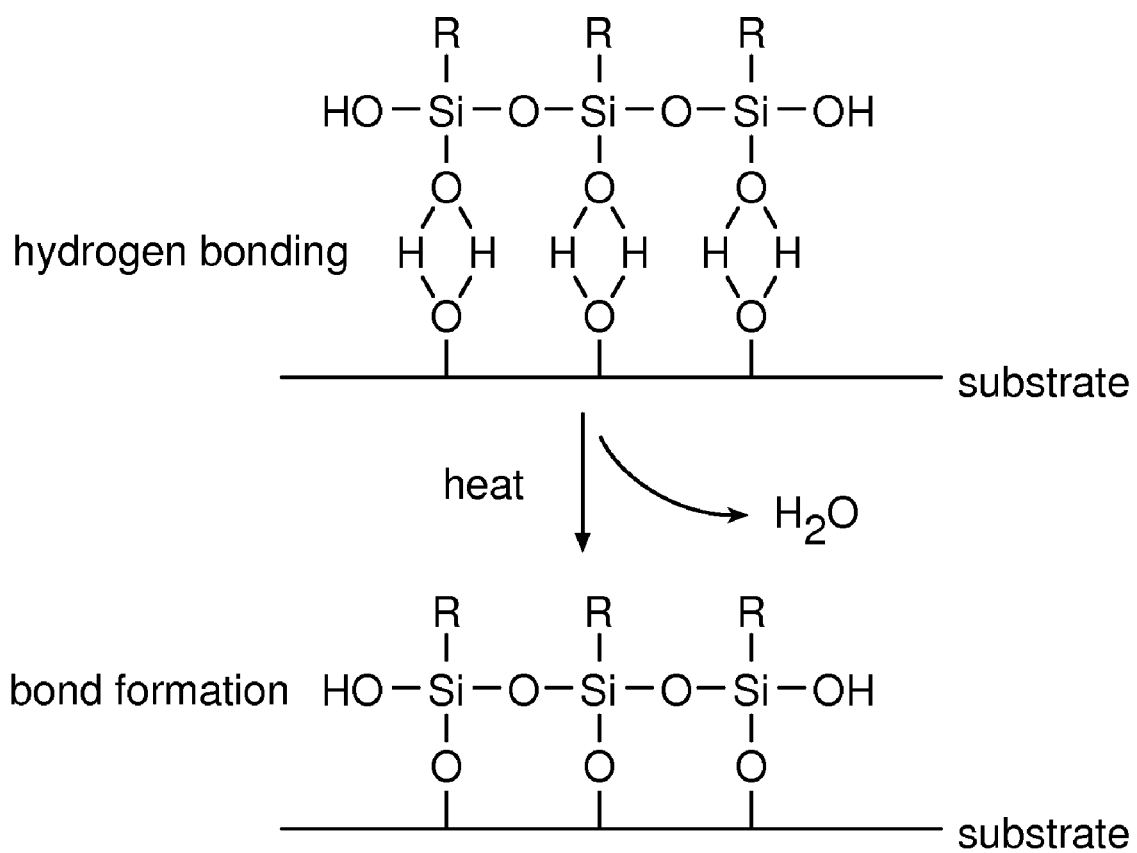
FIG. 3 is a schematic representation of bonding of silane agent to an inorganic substrate.

In one example employing the principles of the present invention, a metal stent is grafted with a bioabsorbable polylactide. It should be understood, however, that the present example may be applied to other surfaces such as glass or ceramic surfaces. The metal surface is activated with silane derivatives, as shown in FIGS. 1-3.

In a particular example, stainless steel stents (316 L) or cobalt chromium (L605) stents were placed in commercially available ENPREP solution (45 g in 750 ml of water) and incubated at 70-100 C for 1 hour. The stents were rinsed in water twice and isopropanol (IPA) twice respectively. Two silane agents that may be employed for this invention can be obtained commercially from Dow Corning with the following catalog numbers: Z6911 for sulfhydryl functional group; and Z-6040 for the silane agent with epoxy functional group. The surface activated stents were then incubated in an IPA and water solution of mixed silane derivatives containing both sulfhydryl group (3-mercaptopropyltrimethoxy-silane) and epoxy groups (Glycidoxypropyltrimethoxysilane, Z-6040 from Dow Corning), for 1 hour under agitation. The silane treated stents are then rinsed with IPA, water and air dried for surface inspection. The silanized surface is further cured in oven at 60-100 C for about 1 hour.

Figure 4:
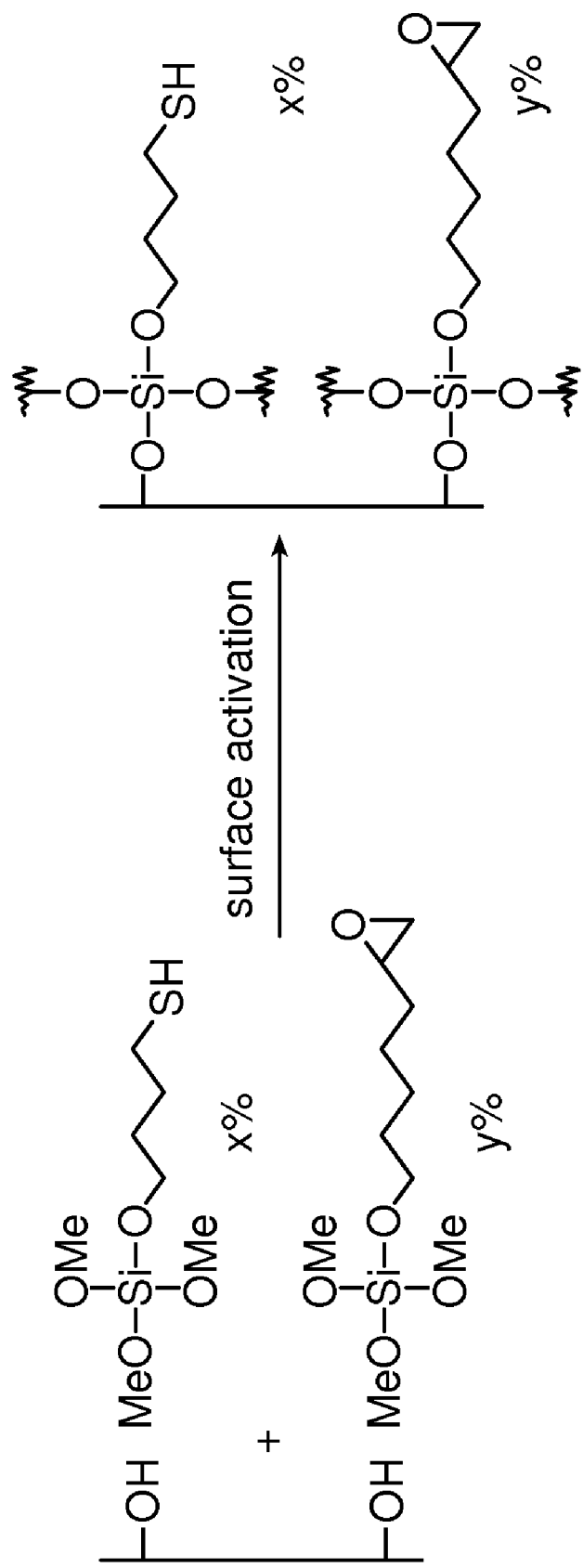
FIG. 4 is a schematic representation of bonding of silane agent containing a sulfhydryl group and an epoxy group to a surface.
Figure 5:
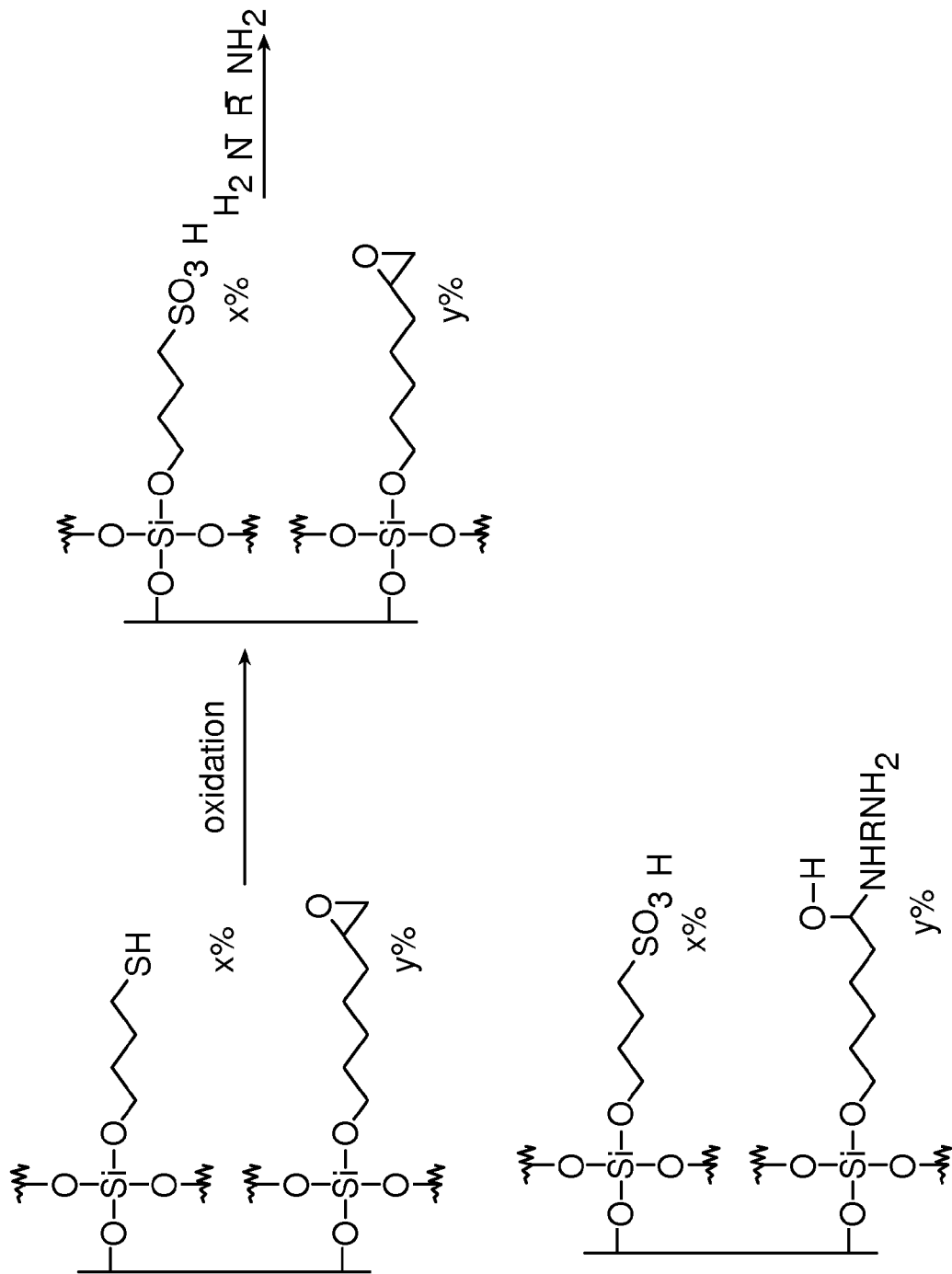
FIG. 5 is a reaction scheme of the conversion of a sulfhydryl group to a sulfonic acid and an epoxide group to multifunctional terminals.
Figure 6:
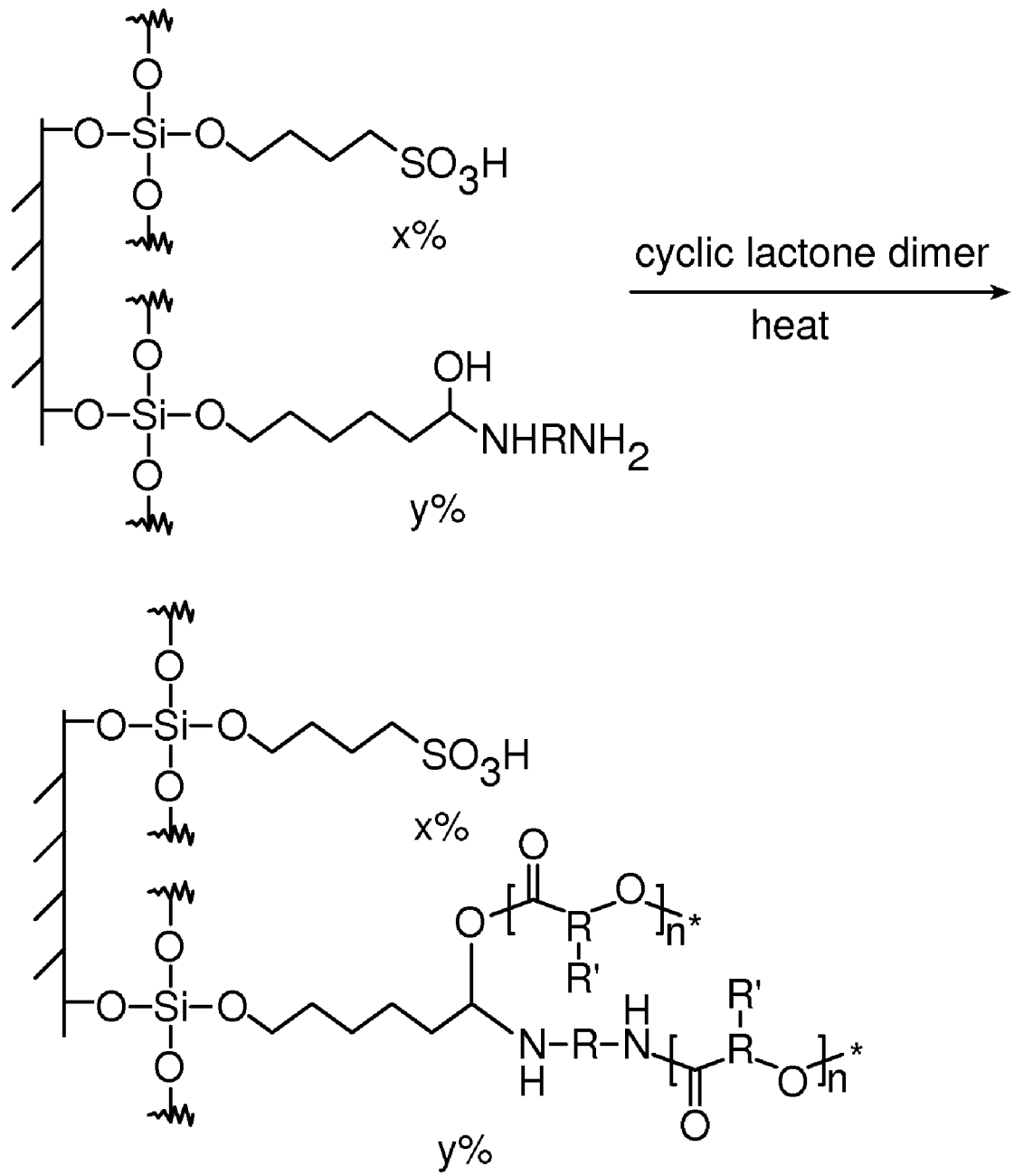
FIG. 6 is a schematic representation of the reaction mechanism and structure involved in ring opening polymerization of a lactone dimer or monomer on the activated silane terminals.

After activation of the surface, the sulfhydryl group was coverted to sulfonic acid, and the epoxy group to a hydroxyl and an amine group, as shown in FIGS. 4-5. The sulfhydryl terminals on the surface can be converted into sulfonic acid by using $H_2O_2$ in an aqueous medium (10 ml methanol/20 ml of 30% $H_2O_2$ solution). The solution is stirred at room temperature for 24 hours. (In the particular example described above, the stents were then washed by copious amounts of de-ionized water.) The conversion of the epoxy group into a dual or multiple functional terminals for subsequent ring opening polymerization is achieved by reacting the epoxy carrying silanized surface with a suitable diol, such as 1,3-propanediol, or a diamine, such as lysine ethylester, in an organic solution. A typical example of the conversion involves a lysine ethylester under reflex conditions in tetrahydrofuran (THF) for 2-4 hours. (In the particular example described above, the stents are then washed with THF and dried in vacuum over night to produce a surface with both sulfonic acid, hydroxyl and amine terminals.) Thereafter, ring-opening polymerization, as shown in FIG. 6, is initiated.

The functionalized stents are then transferred into a glass reactor containing d,l-lactide monomer (for instance, the lactone dimer from Purac USA). The reactor is then degassed and heated to about 120-150 C overnight to complete the graft polymerization on the surface. The reactor is then open and the content washed with THF and dried in vacuum oven before subsequent coating processes. The amount of the grafted poly(d,l-lactide) layer on the stent surfaces can be determined by the weight gain before and after the ring opening polymerization and by analyzing the surface composition using techniques such as time of flight secondary ion mass spectroscopy (TOF-SIMS) and ESCA (Electron Spectroscopy for Chemical Analysis).

Although the present invention has been described above with respect to particular preferred embodiments, it will be apparent to those skilled in the art that numerous modifications and variations can be made to these designs without departing from the spirit or essential attributes of the present invention. Accordingly, reference should be made to the appended claims, rather than to the foregoing specification, as indicating the scope of the invention. The descriptions provided are for illustrative purposes and are not intended to limit the invention nor are they intended in any way to restrict the scope, field of use or constitute any manifest words of exclusion.

I claim:

1. A composition comprising crosslinked silane derivatives linked to a surface having at least two functional terminals comprising an epoxide group and a sulfhydryl group, wherein the sulfhydryl group is oxidized to form sulfonic acid which serves as an in situ catalyst for ring opening polymerization, in suitable solvent or in bulk, to graft a first lactone polymer layer, and a second polymer layer is at least one of deposited, coated or sprayed on top of the first polymer layer, said second polymer layer having a therapeutic agent contained therein, the total thickness of the composition being in the range of about 0.01 to about 100 micrometers and wherein the weight of the therapeutic agent is in the range from about 0.1 to about 500 micrograms per square centimeter of surface area.

2. The composition of claim 1 wherein the therapeutic agent comprises an anti-proliferative agent.

3. The composition of claim 1 wherein the therapeutic agent comprises an anti-inflammatory agent.

4. The composition of claim 1 wherein the therapeutic agent comprises an anti-thrombotic drug.

* * * * *